United States Patent [19]

Steigelmann et al.

[11] Patent Number: 5,300,722
[45] Date of Patent: Apr. 5, 1994

[54] OXYGEN-FREE AROMATIC ALKYLATION PROCESS

[75] Inventors: Edward F. Steigelmann; Maribeth B. Amundsen; Ken Tadano, all of Naperville; Allen I. Feinstein, Wheaton, all of Ill.

[73] Assignee: Amoco Corporation, Chicago, Ill.

[21] Appl. No.: 634,769

[22] Filed: Dec. 27, 1990

[51] Int. Cl.5 ............................................. C07C 2/58
[52] U.S. Cl. ...................................... 585/467; 585/471
[58] Field of Search ................... 585/467, 471; 502/71

[56] References Cited

U.S. PATENT DOCUMENTS 4,459,426  7/1984  Inwood et al. ..................... 585/467
4,891,458  1/1990  Innes et al. ........................ 585/467

Primary Examiner—Asok Pal
Assistant Examiner—P. Achutamurthy
Attorney, Agent, or Firm—Thomas A. Yassen; Richard A. Kretchmer

[57] ABSTRACT

In an aromatic alkylation process, an aromatic hydrocarbon is contacted with an alkylating agent in a reactor vessel in the absence of oxygen in the presence of a silica-containing molecular sieve catalyst under liquid phase alkylation conditions to recover an alkyl-substituted aromatic product from said reactor vessel.

26 Claims, 2 Drawing Sheets

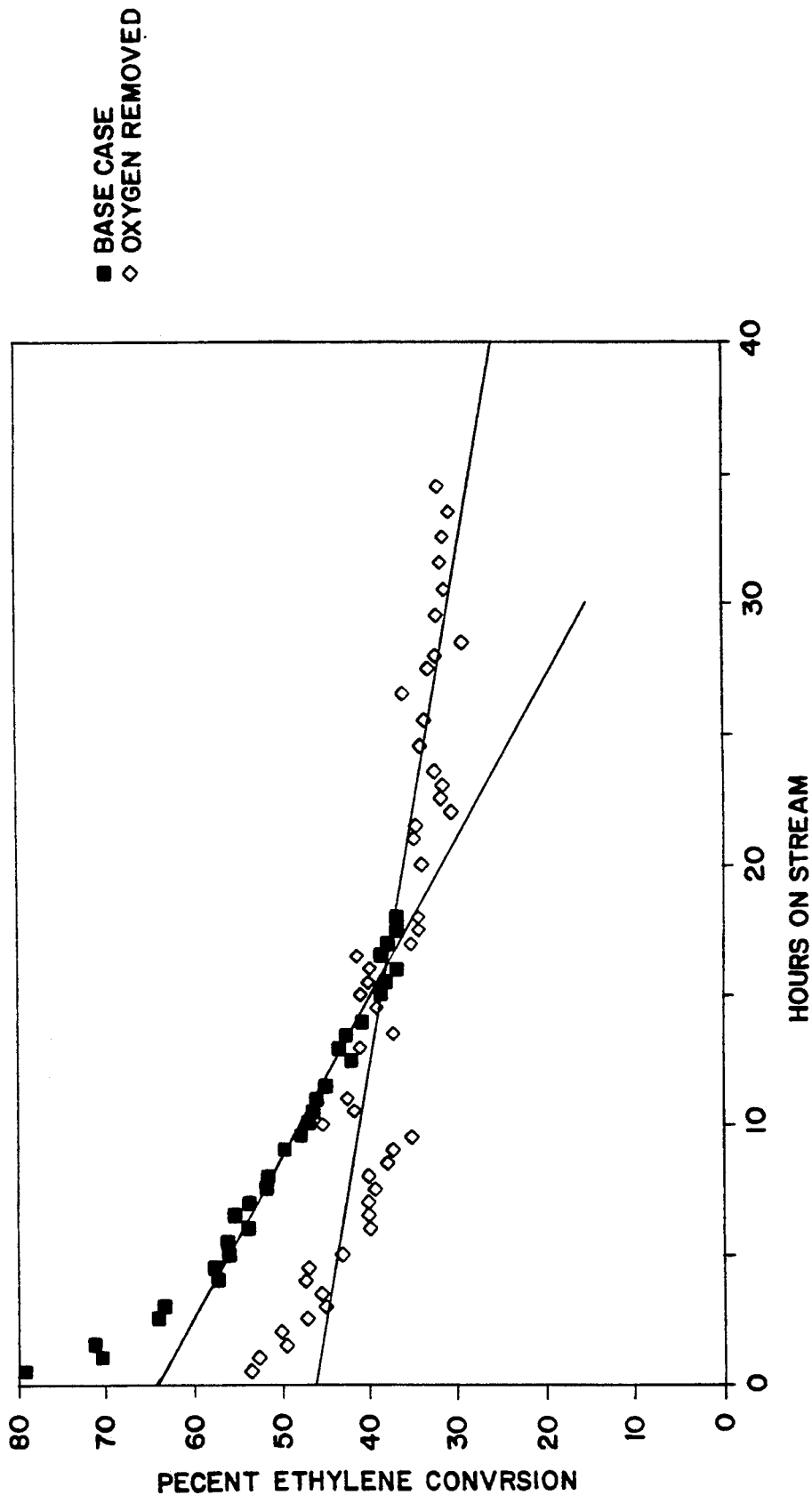

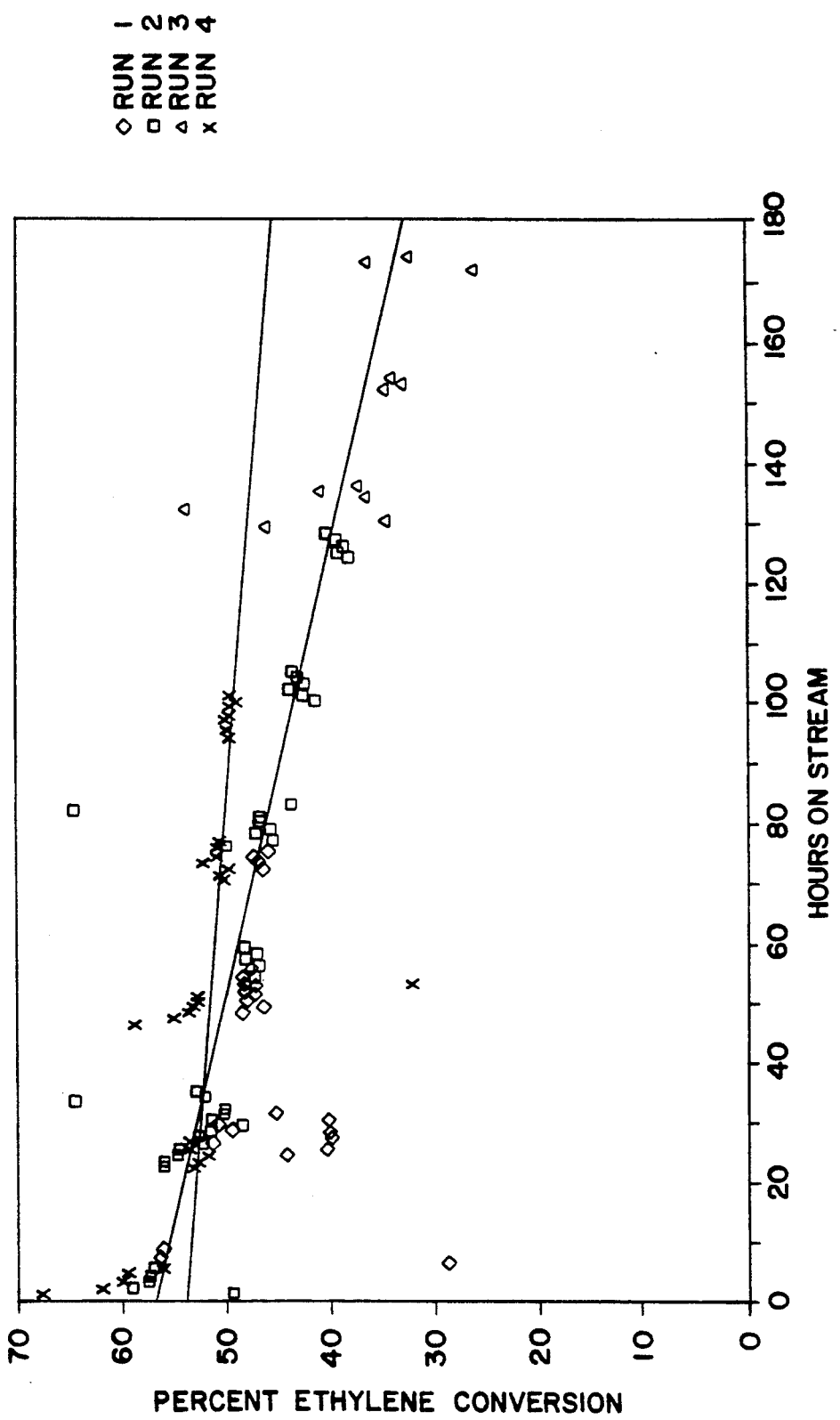

OXYGEN-FREE AROMATIC ALKYLATION PROCESS

FIELD OF THE INVENTION

The invention relates to an aromatic alkylation process comprising the steps of contacting an aromatic hydrocarbon with an alkylating agent in a reactor vessel in the absence of oxygen in the presence of a silica-containing molecular sieve catalyst under liquid phase alkylation conditions, and recovering an alkyl-substituted product from said reactor vessel.

BACKGROUND OF THE INVENTION

Hydrocarbon conversion processes, particularly alkylation of aromatic hydrocarbons, are the foundation for the production of an assorted variety of useful petrochemicals. For instance, ethylbenzene and ethyltoluene, as well as other alkyl-substituted aromatics, are beneficial as feedstocks for the production of a variety of styrenic polymer materials, cumene, and detergent alkylates. Alkyl-substituted aromatics are also useful as high octane transportation fuels. The use of alkyl-substituted aromatics as blending agents for gasoline expands product volume and increases octane values. Aromatic alkylation processes also provide an economic method of reducing benzene content in gasoline.

In the past, alkylation processes have employed acidic catalysts such as $AlCl_3$, $FeCl_3$, $SbCl_5$, $BF_3$, $ZnCl_2$, $TiCl_4$, HF, $H_2SO_4$, $H_3PO_4$, $P_2O_5$ and the like. Reactions using these catalysts are generally carried out at low temperatures and, in particular, when a Friedel-Craft catalyst is employed, in the presence of a hydrogen halide, such as HCl.

There are numerous problems associated with the use of these acidic catalysts in an alkylation process. First, these catalysts are very corrosive, thereby requiring the use of exotic materials for process equipment. Second, the catalyst consumption and the regeneration costs are high. Third, the yields of alkylate boiling in the gasoline range are low. Fourth, complicated separations and recycle of feed can be required. Fifth, these catalysts tend to polymerize the olefinic reagents, thus minimizing available starting materials.

Many of these problems have been avoided by using synthetic or natural zeolite materials as alkylation catalysts. Zeolitic materials are porous crystalline aluminosilicates having a definite crystalline structure within which there are a large number of smaller cavities which can be interconnected by a number of even smaller channels. Since the dimensions of these pores are such that molecules of a certain dimension are accepted for adsorption while larger molecules are rejected, these materials have come to be known as "molecular sieves."

A particular type of molecular sieve useful in aromatic alkylation reactions is a crystalline aluminosilicate zeolite. Crystalline aluminosilicate zeolites are composed of a rigid three-dimensional framework of $SiO_4$ and $AlO_4$ in which the tetrahedra are cross-linked by the sharing of oxygen atoms. The electrovalence of the tetrahedra containing aluminum is balanced by the inclusion in the crystal of a cation, such as an alkali metal or an alkaline earth metal. Since these cations are exchangeable, it is possible to vary the properties of a particular aluminosilicate by selection of a suitable cation.

The use of crystalline aluminosilicates in aromatic alkylation processes is well known in the art. In U.S. Pat. No. 2,904,607 there is disclosed a process for alkylating aromatics with olefins in the presence of a crystalline metallic aluminosilicate having a uniform pore opening of about 6–15 Angstroms. In U.S. Pat. No. 3,251,897 there is disclosed a process for alkylating aromatics with a crystalline aluminosilicate which contains rare earth metal cations and a uniform pore volume of at least 6 Angstroms.

While the use of crystalline aluminosilicate zeolite catalysts in aromatic alkylation processes represents a distinct improvement over Friedel-Craft catalysts, zeolite catalysts have the disadvantage of producing unwanted quantities of impurities. They also deactivate at a rapid rate, particularly in vapor phase reaction zones. Consequently, the industry began treating zeolites to specifically address these deactivation and selectivity problems. In U.S. Pat. No. 2,897,246, there is disclosed heating a crystalline aluminosilicate in the presence of water vapor at a temperature of 400–900 deg C prior to using it in an alkylation process. In U.S. Pat. No. 3,631,120, there is disclosed ammonium-exchanging a crystalline aluminosilicate to achieve a silica-to-alumina molar ratio of 4.0–4.9 prior to using it in an aromatic alkylation process. Other methods of treating a crystalline aluminosilicate for use in an aromatic alkylation process include steaming and ammonium-exchanging the zeolite (3,641,177), rare earth-exchanging the zeolite in the presence of sulfur dioxide (4,395,372), partially collapsing the zeolite to reduce crystallinity (4,570,027), contacting the zeolite with aluminum chloride vapor (4,575,573), increasing the total amount of lattice metal in the zeolite (4,665,255), reacting the zeolite with an acidic inorganic oxide in the presence of water (4,665,253), or depositing carbonaceous material on the zeolite (4,798,816).

New crystalline aluminosilicates were also developed to address these selectivity and deactivation problems. U.S. Pat. Nos. 4,393,263, 4,291,185, 4,387,259, 4,393,262, and 4,469,908 disclose the use of ZSM-12 in an aromatic alkylation process. U.S. Pat. No. 4,547,605 discloses the use of ZSM-23 in an aromatic alkylation process. U.S. Pat. No.4,717,780 discloses the use of ZSM-58 in an aromatic alkylation process.

U.S. Pat. No. 4,185,040 discloses that the selectivity and deactivation problems associated with the use of crystalline aluminosilicates can be addressed by shaping the extrudates to give a high ratio of external surface area to crystal pore volume. Crystal pore diameter is defined as 5–15 Angstroms.

The process conditions used during aromatic alkylation can affect the performance of a crystalline aluminosilicate zeolite catalyst. For example, vapor phase aromatic alkylation processes, such as those disclosed in U.S. Pat. Nos. 3,751,504 and 3,751,506, generally have high conversions due to greater ease in the diffusion of the vapor reactants into the micropores of the crystalline aluminosilicate, but high catalyst deactivation rates due to olefins attaching to the active sites of the zeolite catalyst and deactivating the catalyst by coke deposition. On the other hand, liquid phase aromatic alkylation processes, such as those described in U.S. Pat. Nos. 3,251,897 and 3,631,120, generally have lower conversion rates due to diffusional limitations, and also lower catalytic deactivation rates due to aromatics preferentially occupying the active sites of the zeolite catalyst, thereby preventing the olefins from deactivating the catalyst.

It is therefore desirable to provide an improved aromatic alkylation process which overcomes most, if not all, of the preceding problems.

SUMMARY OF INVENTION

In its broadest aspect, the present invention is an aromatic alkylation process comprising the steps of contacting an aromatic hydrocarbon with an alkylating agent in a reactor vessel in the absence of oxygen in the presence of a silica-containing molecular sieve catalyst under liquid phase alkylation conditions, and recovering an alkyl-substituted aromatic product from said reactor vessel. It has been discovered that effecting an aromatic alkylation reactor in the absence of oxygen lowers the catalyst deactivation rate lower than typical liquid phase aromatic alkylation processes which operate in the presence of oxygen.

In one embodiment, the present invention is an aromatic alkylation process comprising the steps of purging a reactor vessel having a silica-containing molecular sieve catalyst disposed therein with an oxygen-free inert purge gas; continuously feeding a deoxygenated aromatic hydrocarbon into said reactor vessel; continuously feeding a deoxygenated alkylating agent into said reactor vessel; contacting said aromatic hydrocarbon with said alkylating agent in said reactor vessel in the absence of oxygen in the presence of a silica-containing molecular sieve catalyst under liquid phase alkylation conditions; and recovering an alkyl-substituted aromatic product from said reactor vessel.

In another embodiment, the present invention is an aromatic alkylation process comprising the steps of purging a reactor vessel having an alkylation catalyst comprising beta zeolite in an alumina matrix with a purge stream consisting essentially of nitrogen; continuously feeding a deoxygenated aromatic hydrocarbon having at least one member selected from the group consisting of benzene, toluene, xylenes, and $C_9$ hydrocarbons into said reactor; continuously feeding a deoxygenated olefinic hydrocarbon comprising ethylene and propylene into said reactor; contacting said aromatic hydrocarbon with said olefinic hydrocarbon in said reactor in the absence of oxygen in the presence of said alkylation catalyst under liquid phase alkylation conditions; and recovering an alkyl-substituted aromatic product from said reactor vessel.

DESCRIPTION OF THE DRAWING

FIG. 1 is a plot of hours on stream versus percent of ethylene converted during aromatic alkylation in the presence of an ultrastable Y zeolite catalyst at 400 deg F, 300 psig, and an A/O ratio of 2.0.

FIG. 2 is a plot of hours on stream versus percent of ethylene converted during aromatic alkylation in the presence of a beta zeolite catalyst at 400 deg F, 300 psig, and an A/O ratio of 2.0.

DETAILED DESCRIPTION OF THE INVENTION

Broadly, the present invention is directed to an aromatic alkylation process comprising contacting an aromatic hydrocarbon with an alkylating agent in a reactor vessel in the absense of oxygen in the presence of an alkylation catalyst comprising a silica-containing molecular sieve in a porous refractory inorganic oxide matrix under liquid phase alkylation conditions, and recovering an alkyl-substituted aromatic product from said reactor vessel.

Catalysts suitable for use in the present invention can be any silica-containing molecular sieve including, but not limited to, aluminosilicates, borosilicates, gallosilicates, and chromosilicates.

The preferred silica-containing molecular sieves are crystalline aluminosilicate zeolites which are based on an infinitely extending, three-dimensional network of $AlO_4$ and $SiO_4$ tetrahedra linked by the sharing of oxygen atoms. Chemically, the structural formula of a crystallographic unit cell of a zeolite may be expressed in terms of oxides,

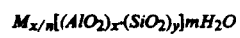

$$M_{x/n}[(AlO_2)_x(SiO_2)_y]mH_2O$$

where M is the cation of valence n, m is the number of water molecules, and the sum of x and y is the total number of tetrahedra in the unit cell. The ratio of y/x can vary depending on the structure. The zeolite can be naturally-occurring or synthetic. Among the naturally-occurring zeolites which can be employed are faujasite, climoptolite, mordenite, and clachiasdite. Synthetic zeolites suitable for use in the present invention include X zeolite, Y zeolite, beta zeolite, L zeolite, and omega zeolite, preferably beta zeolite, optimally a beta zeolite having a sodium concentration of less than about 500 ppm by weight of the zeolite, preferably less than about 150 ppm by weight.

In addition to a silica-containing molecular sieve, the catalyst of the present invention further comprises a porous refractory inorganic oxide matrix or binder which is combined, dispersed, or otherwise intimately admixed with the zeolite in order to provide the physical strength and attrition resistance required in industrial use. Suitable inorganic binders include alumina, silica, clays, bauxite, zirconium oxide, hafnium oxide, titanium dioxide, zinc oxide, and magnesia. Suitable zeolite-binder composites contain about 1–99 wt % of a zeolite component, preferably about 70–95 wt % based on the weight of the zeolite-binder composite. The binder component makes up the remainder of the composite.

Suitable methods for compositing the zeolite materials with the binder can be found in U.S. Pat. Nos. 4,808,763 and 4,738,768, which are herein incorporated by reference.

Preferably, the catalyst of the present invention has in part a pore volume of about 0.25–0.50 cc/g in pores having a radius greater than 450 Angstroms and a catalyst particle diameter cf about ⅛ to 1/200 inches, preferably ⅛ to 1/64 inches.

The catalyst can be disposed in any reactor vessel known to those skilled in the art to be suited for hydrocarbon conversion including, but not limited to, reactors having fixed-bed, fluidized-bed, ebullated-bed, and moving-bed catalyst zones. In a preferred embodiment, the catalyst can be employed in a plurality of solid porous containers, examples of which are disclosed in U.S. Pat. Nos. 4,215,011, 4,302,356, and 4,443,559, disposed in a reactive-distillation zone of the reactor vessel. The use of the porous containers allows for the increased void volume within the reactor, thereby reducing the pressure drop across the reactor. The use of a reactive-distillation zone in the reactor vessel has the added benefit of immediately removing by fractionation desirable monoalkylated aromatics from the reaction zone, thereby reducing the formation of undesirable polyalkylated aromatics.

In a preferred embodiment, the catalyst of the present invention is activated in the reactor vessel prior to initiating the aromatic alkylation reaction in the following manner: 1) contacting the catalyst with a gaseous stream comprising about 1-5 mole % $O_2$ and nitrogen at a rate of about 100 ml/min per gram of catalyst at room temperature while increasing the temperature to an intermediate temperature of about 200-600 deg F, preferably 300-500 deg F at a rate of heating of about 0.1-10 deg F/min, preferably about 0.5-5 deg F/min; 2) maintaining this intermediate temperature for a period of time sufficient to drive off a swmtantial amount of water or other adsorbed material, preferably about 4-6 hr; 3) increasing the temperature of said gaseous stream to an activation temperature of about 700-1100 deg F, preferably about 800-1000 deg F at rate of heating of about 0.1-10 deg F/min, preferably about 0.5-5 deg F/min; 4) maintaining this activation temperature for about 4-6 hr; 5) contacting the catalyst with a gaseous stream comprising oxygen and nitrogen at said activation temperature for about 16-24 hr, said gaseous stream having an initial oxygen concentration of about 5 mole %, said oxygen concentration increasing in increments of 5 mole % every 4-6 hr until a final oxygen concentration of about 20 mole % is achieved; 6) cooling the catalyst to room temperature and purging the reactor with a gaseous stream comprising nitrogen; 7) contacting the catalyst with a gaseous stream comprising hydrogen at about 300 ml/min while raising the temperature of the gaseous stream from room temperature to about 700-1100 deg F, preferably about 800-1000 deg F and maintaining such a temperature for about 4-6 hr; 8) cooling the catalyst down to room temperature.

Suitable aromatic hydrocarbons useful in this invention comprise benzene, toluene, ortho-xylene, metaxylene, pars-xylene, ethylbenzene, ortho-ethyltoluene, meta-ethyltoluene, para-ethyltoluene, 1,2,3-trimethylbenzene, 1,2,4-trimethylbenzene, 1,3,5-trimethylbenzene or mesitylene, normal propylbenzene and isopropylbenzene. Higher molecular weight alkylaromatic hydrocarbons are also suitable and include aromatic hydrocarbons such as are produced by the alkylation of aromatic hydrocarbons with olefin polymers. Examples of such products are hexylbenzene, nonylbenzene, dodecyltoluene, and pentadecyltoluene. Other suitable alkylatable aromatic hydrocarbons include those having two or more aryl groups, such as diphenyl, diphenylmethane, triphenyl, and triphenylmethane. Examples of other alkylatable aromatic hydrocarbons within the scope of this invention include materials containing condensed benzene rings, such as naphthalene, alpha-methylnaphthalene, beta-methylnaphthalene, anthracene, phenanthrene, and naphthacene. Of the above aromatic hydrocarbons for use in the present invention, benzene, toluene, xylenes, and $C_9$ hydrocarbons are preferred.

A suitable source of aromatic hydrocarbons is a refinery total reformate stream. In general, such a stream has about 25 to 35 wt % paraffins, 0.5-2 wt % naphthenes, and 60-80 wt % aromatics. A typical refinery total reformate stream has a composition in mole percent of about: 0.5% $C_4$ paraffins, 8.9% $C_5$ paraffins, 13.2% $C_6$ paraffins, 5.5% $C_7$ paraffins, 0.8% $C_8$ paraffins, 0.1% $C_9$ paraffins, 0.3% $C_5$ naphthenes, 0.3 $C_6$ naphthenes, 0.2% $C_7$ naphthenes, 0.1% $C_8$ naphthenes, 8.4% $C_6$ aromatics, 20.3% $C_7$ aromatics, 19.8% $C_8$ aromatics, 13.2% $C_9$ aromatics, 6.5% $C_{10}$ aromatics, and 1.9% $C_{11}+$ aromatics. Preferably, the aromatic source is a light fraction of the total reformate stream. In general, such a stream has about 40-60 wt % paraffins, 1-3 wt % naphthenes, and 40-50 wt % aromatics. A typical light refinery reformate stream has a composition in mole percent of about 1.6% $C_4$ paraffins, 12.2% $C_5$ paraffins, 20.6% $C_6$ paraffins, 12.8% $C_7$ paraffins, 5.5% $C_8$ paraffins, 0.5% $C_9$ paraffins, 0.6% $C_5$ naphthenes, 0.7% $C_6$ naphthenes, 0.4% $C_8$ naphthenes, nil $C_9$ naphthenes, 10.9% $C_6$ aromatics, 28.7% $C_7$ aromatics, and 4.6% $C_8$ aromatics.

Alkylating agents suitable for use in the present invention are olefins, alcohols, alkenes, alkynes, aldehydes, ethers, acetylenes, and any other acrylic compounds having at least one reactive alkyl radical. Suitable alcohols are methanol, ethanol, n-propanol, and isopropanol. The olefins can be $C_2$ to $C_{20}$ olefins, preferably $C_2$-$C_{12}$ olefins, including normal and branched forms thereof. For example, suitable olefins are ethylene, propylene, butylene, isobutylene, 1-pentene, 1-hexene, 2-hexene, cyclohexene, methyl cyclohexene, 2,3-dimethyl-1-pentene, 1-octene, diisobutylene, 1-nonene, 1-decene, dodecene and the like. In a preferred embodiment the olefin is a $C_2$-$C_4$ olefin. The preferred alkylating agents are ethylene and propylene.

The present invention can be practiced with alkylating agents wherein the ethylene and propylene olefinic hydrocarbons are present in gas streams. The gas streams are present in petroleum refineries from various refinery installations including thermal cracking units, catalytic cracking units, thermal reforming units, coking units, and polymerization units. A typical analysis in mole percent for a suitable refinery off-gas is as follows: 4.0% nitrogen, 0.2% carbon monoxide, 5.4% hydrogen, 37.8% methane, 10.3% ethylene, 24.7% ethane, 6.5% propylene, 10.7% propane, and 0.5% $C_4$ hydrocarbons.

A suitable aromatic to alkylating agent ratio in the reaction zone can be greater than about 0.8 for reactive-distillation processes, preferably greater than about 1.5 for fixed-bed processes.

An essential feature of the present invention is contacting the aromatic hydrocarbon with the alkylating agent in the absence of oxygen. "In the absence of oxygen" is defined as a molecular oxygen concentration of less than about 1 ppm by weight, preferably less than about 0.1 ppm by weight, more preferably less than 0.01 ppm by weight, most preferably less than about 0.001 ppm by weight. It has been discovered that effecting an aromatic alkylation reaction in the absence of oxygen reduces the catalyst deactivation rate.

Typically, oxygen enters the alkylation reaction zone from the reactor, catalyst, and feedstreams. For example, where the source of the feedstreams is a refinery, typical oxygen concentration in the feedstreams can be 15-30 ppm. Accordingly, in a preferred embodiment, the present invention encompasses the steps of monitoring and regulating the oxygen concentration in the reactor, catalyst, and feedstreams.

Oxygen present in the reactor can be reduced by purging the reactor vessel (including any feed lines leading thereto) with an oxygen-free inert purge gas. "Oxygen-free" is defined as an oxygen concentration of less than about 1 ppm by weight, preferably less than about 0.1 ppm by weight, more preferably less than about 0.01 ppm by weight, most preferably less than about 0.001 ppm by weight. Suitable purge gases include, but are not limited to, argon, nitrogen, and hydrogen. In a preferred embodiment, the purge occurs while the catalyst of the present invention is disposed in the reactor vessel.

Oxygen present in the feedstreams can be removed by any deoxygenation method known to those skilled in the art. Accordingly, in a preferred embodiment, a deoxygenated aromatic hydrocarbon is contacted with a deoxygenated alkylating agent to produce an alkyl-substituted aromatic. "Deoxygenated" is defined as an oxygen concentration of less than about 1 ppm by weight, preferably less than about 0.1 ppm by weight, more preferably less than about 0.01 ppm by weight, most preferably less than about 0.001 ppm by weight.

Suitable methods for deoxygenating the reactant feed streams include, but are not limited to, sparging a liquid feed stream with with an oxygen-free inert sparge gas, passing a liquid or gaseous feed stream through an oxygen adsorbent, contacting the feed stream with a hydrogen-containing gas, contacting the feed stream with a hydrocarbon-containing gas, or any combination thereof.

In one embodiment, a liquid aromatic hydrocarbon can be sparged with an oxygen-free inert sparge gas until the oxygen level has been reduced to less than about 0.1–0.5 ppm by weight. Suitable inert gases include, but are not limited to, argon, hydrogen, and nitrogen. A suitable sparge rate can be about 10–30 ml/min. The sparged liquid aromatic can be continuously fed through an oxygen detector, such as an orbisphere oxygen detector, to monitor the oxygen concentration.

In another embodiment, a liquid or gaseous reactant feed stream can be contacted with an oxygen adsorbent until the oxygen concentration of the feed stream is less than about 0.1–0.03 ppm by weight. A suitable oxygen adsorbent can be CuO (that has been activated by reduction with hydrogen) on an inorganic oxide support. Additionally, water adsorbents, such as molecular sieves, can be used to reduce the water content of the feed reactants. The oxygen and water adsorbents can be activated by flowing a gaseous stream comprising 5 mole % hydrogen through the adsorbent beds while raising the temperature to about 520 deg F and 800 deg F, respectively. Each adsorbent bed can be kept at these temperatures for at least about 10 hr.

Another essential feature of the present invention is carrying out the aromatic alkylation reaction under liquid phase alkylation conditions. "Liquid phase alkylation conditions" is defined as a continuous liquid phase in the catalyst zone of the reactor vessel of the present invention, or a liquid phase having a continuous flow of vapor bubbling up through the catalyst zone of said reactor vessel. The source of the vapor can be external to the reactor vessel, for example, a gaseous alkylating agent feed stream, or internal to the reactor vessel, for example, vapor generated from a reboiler used in conjuction with reactor vessel having a reactive-distillation catalyst zone.

Other process conditions suitable for use in the present invention include a temperature of about 300–600 deg F, preferably about 300–450 deg F, a pressure of about 1–100 atms, preferably about 10–30 atms, and a weight hourly space velocity of about 0.02–20 $hr^{-1}$.

EXAMPLE 1

In Example 1, an oxygenated (oxygen concentration of about 15 ppm by weight) liquid aromatic hydrocarbon was contacted with a gaseous olefinic hydrocarbon in the presence of a crystalline zeolite catalyst under liquid phase conditions. The purpose was to evaluate the effect of oxygen on catalyst deactivation rate.

The catalyst used was an ultrastable Y zeolite similar in composition to the commercially available LZY-82 which is produced by Union Carbide. The catalyst had an initial particle diameter of 1/32 inches and was ground and sieved to a particle diameter of 20/40 mesh (1/40 inches). After being ground and sieved, the catalyst was calcined in a furnace at 950 deg F for 4 hr and cooled in a vacuum desiccator to room temperature. The catalyst possessed a macropore (radius greater than 450 Angstroms) volume of 0.26 cc/gm.

The catalyst was disposed in a 3.25 inch catalyst zone of an 18 inch by ¼ inch o.d. stainless steel, tubular-shaped reactor. The catalyst zone contained 1.8 gm of catalyst and sufficient 20/40 mesh (1/40 inch) PHF alumina to bring the total volume of the catalyst zone to 6.0 cc. The space directly above and below the catalyst zone was packed with 14-20 mesh alpha alumina. The ends of the reactor were packed with glass wool.

The catalyst was pretreated in the reactor by heating it to 950 deg F in a gaseous stream consisting essentially of 2 mole % oxygen in nitrogen to dry the catalyst and to burn off any carbonaceous residue. Next, the catalyst in the reactor was contacted with hydrogen at 950 deg F for about 16 hr.

To begin the experiment, the reactor and the catalyst were flushed with a gaseous stream consisting essentially of nitrogen at room temperature. The reactor was then pressurized and the reactor temperature was raised to 350 deg F. The reactor was brought on stream by feeding a liquid aromatic hydrocarbon consisting essentially of 50 mole % toluene and 50 mole % tetradecane at a rate of 42 ml/hr through a substantially deactivated guard bed containing oxygen and water adsorbents and up through the catalyst bed using a 350 ml ISCO high pressure pump while nitrogen was flowing up through the reactor. The oxygen concentration of the liquid feed to the guard beds was estimated to be about 15 ppm by weight. The guard bed was a stainless steel 18 inch by ¼ inch tube that was packed at the top with an oxygen adsorbent known as Dow Q-5 and a water adsorbent known as a 4A molecular sieve. Dow Q-5 is a solid adsorbent which composed of alumina (89.2 wt %), CuO (10 wt %), NiO, CoO, and MnO. The oxygen concentration of the guard bed effluent was estimated to be about 10 ppm. The guard bed was ineffective at removing a significant amount of oxygen from the liquid stream. Later it was discovered that the adsorbents in the guard bed were deactivated in need of regeneration.

After the reactor had stabilized, a gaseous alkylating agent consisting essentially of 80 mole % methane and 20 mole % ethylene was fed into the reactor at a rate of 182 ml/min (at standard temperature and pressure) and the nitrogen flow was turned off. Other process conditions included a reactor pressure of 300 psig and an average temperature across the catalyst bed of 400 deg F.

Both gas and liquid samples were collected every ¼ hr and both were analyzed using a gas chromatograph.

The data for percent ethylene conversion with time on stream is given in FIG. 1 (squares). The initial ethylene conversion was about 80%. After an extrapolated 30 hours on stream, the ethylene conversion had dropped to less than 20%. The equation for deactivation as determined by linear regression is shown below:

% Conv. = 63.81 − (1.05) HOS where HOS was hours on stream. Accordingly, the catalyst deactivation rate was (1.05) (% Cony/HOS).

EXAMPLE 2

In Example 2, a deoxygenated (oxygen concentration estimated to be less about 0.01 ppm by weight) liquid aromatic hydrocarbon was contacted with a gaseous olefinic hydrocarbon in the presence of a crystalline aluminosilicate zeolite catalyst under liquid phase conditions. The purpose of Example 2 was to evaluate the effect of oxygen on catalyst deactivation rate.

For Example 2, the catalyst charge of Example 1 was regenerated in the reactor of Example 1 by contacting the catalyst with a gaseous stream consisting essentially of 2 mole % oxygen in nitrogen at atmospheric pressure and 200 ml/min until essentially no carbon monoxide or carbon dioxide was detected in the effluent. The catalyst was cooled to room temperature.

To begin the experiment, the reactor and catalyst were flushed with a gaseous stream consisting essentially of nitrogen at room temperature. The reactor was pressurized with a gaseous stream consisting essentially of hydrogen and then slowly depressurized. The pressurizing cycle was repeated 3 times to lower the reactor oxygen levels. Next the reactor was heated to 950 deg F using a gaseous stream consisting essentially of hydrogen at 300 psig to remove any adsorbed oxygen on the catalyst.

The reactor was then cooled to an operating temperature of 350 deg F and brought on stream as in Example 1, with one exception. The exception being that the liquid aromatic hydrocarbon feed was routed through a guard bed containing regenerated oxygen and water adsorbents prior to being introduced into the reactor. The regeneration procedure comprised contacting the water and oxygen adsorbents with a gaseous stream comprising 5 mole % hydrogen in nitrogen at atmospheric conditions at a rate of 200 ml/min at 520 deg F for a period of time sufficient to reduce the $CO_2$ and CO detected in the guard bed effluent to a negligible amount. The regenerated guard bed was able to reduce the oxygen concentration in the feed from an estimated 15 ppm by weight to an estimated 0.01 ppm by weight. After the reactor had stabilized, the gaseous alkylating agent of Example 1 was introduced to the reactor and the nitrogen flow turned off. Other reactor process conditions were the same as Example 1.

As in Example 1, both gas and liquid samples were collected every ½ hr and both were analyzed using a gas chromatograph.

The data for ethylene conversion with time on stream is given in FIG. 1 (diamonds). The initial conversion was about 55%. After 35 hours on stream, the ethylene conversion had dropped to about 30%. A least squared curve through these data points is given by:

% Conv. = 48.74 − 0.15 (HOS)

where HOS is hours on stream.

A comparison of Examples 1 and 2 show that the lower the oxygen concentration in the liquid aromatic hydrocarbon feed the lower the catalyst deactivation rate. In Example 1, where the concentration of oxygen in the liquid aromatic hydrocarbon feed to the reactor was estimated to be about 10 ppm by weight, the catalyst deactivation rate was (1.05) (% Cony)/HOS. In comparison, in Example 2, where the oxygen concentration in the liquid aromatic hydrocarbon feed was estimated to be about 0.01 ppm, the deactivation rate was (0.15) (% Cony)/HOS. This represented a decrease in the deactivation rate of a factor of 7.

EXAMPLE 3

In Example 3, an oxygenated (oxygen concentration measured to be about 15 ppm by weight) liquid aromatic hydrocarbon was contacted with a gaseous olefinic hydrocarbon in the presence of a crystalline aluminosilicate zeolite catalyst under liquid phase conditions. The purpose of Example 3 was to further evaluate the effect of oxygen on catalyst deactivation rate.

The catalyst used was a beta zeolite provided by PQ Corporation as 1/16 inch extrudates and was ground and sieved to 20–40 mesh prior to being disposed in the reactor. This catalyst contained 80 wt % zeolite and 20 wt % alumina binder, and had a sodium concentration cf 140 ppm. The catalyst zone of the reactor of Example 1 was loaded with 3.38 gm of the beta catalyst. The packing above and below the catalyst zone was the same as in Example 1.

The catalyst was pretreated in the following manner:
1) 2% oxygen in nitrogen flowed through the reactor at the rate of 300 ml/min.
2) The temperature of the reactor was raised at the rate of 1 deg F/min to 400 deg F where it was held for 4 hours, after which the temperature was raised to 900 deg F at the rate of 1 deg F/min. it was held at this temperature for 6 hours.
3) The reactor was cooled to room temperature and the gas in the reactor was purged with nitrogen.
4) Next, hydrogen flowed through the reactor at 300 ml/min and the temperature of the reactor was raised to 900 deg F at the rate of 1 deg F/min. The temperature was kept at 900 deg F for 6 hours after which the unit was cooled to room temperature.

The reactor was brought on stream by feeding a liquid aromatic feed consisting essentially of 50 volume % toluene and 50 volume % tetradecane at a rate of 42 ml/hr up through the catalyst bed. The oxygen concentration of this liquid feed was measured at about 15 ppm. After the reactor had stabilized, a gaseous stream consisting of 80 mole % methane and 20 mole % ethylene was fed upwardly through the reactor at a rate of 182 mi/min (at standard temperature and pressure). Other process conditions included a reactor pressure of 300 psig and an average temperature across the catalyst bed of 400 deg F.

Both gas and liquid samples were collected every ½ hr and both were analyzed using a gas chromatograph.

The data for percent ethylene conversion with time on stream is given in FIG. 2, run 1 (diamonds). The initial ethylene conversion was about 57%. After about 75 hr on stream the ethylene conversion had dropped to about 47%.

EXAMPLE 4

In Example 4, an oxygenated (oxygen concentration of about 15 ppm by weight) liquid aromatic hydrocarbon was contacted with a gaseous olefinic hydrocarbon in the presence of a crystalline zeolite catalyst under liquid phase alkylation conditions. In Example 4, the purpose, catalyst, reactor, and test conditions were the same as in Example 3, except there were changes made in the catalyst pretreatment, the liquid feed rate, and gaseous composition near the end of the test. More detail will be provided below.

The catalyst was pretreated using the same procedure as Example 3, except an additional step was added after step 2 to regenerate the catalyst. In this additional step, the percent oxygen in the gas was slowly raised stepwise until pure air was used. More specifically, the concentration of the oxygen was increased from 2 to 5 mole % and then to 20 mole % in increments of 5 mole % every 4 hr.

The catalyst was put on stream for about 130 hr under the same reactor conditions as Example 3. Then the liquid stream was slowed to 12 ml/hr and hydrogen was substituted for the gaseous hydrocarbon stream for the next 50 hr.

The data for percent ethylene conversion with time on stream is given in FIG. 2. Run 2 represents the first 130 hr and run 3 represents the final 50 hr where the aromatic hydrocarbon liquid rate was slowed down and hydrogen was substituted for the gaseous hydrocarbon stream. Although there appeared to be a slight reactivation of the catalyst performance for the first few hours of run 3, the catalyst deactivation followed the same trend as established in run 2. That trend as calculated by least squares regression was as follows:

$$\% \ Conv. = 56.9 - 0.134 * HOS$$

where HOS was the hours on stream. The catalyst deactivation rate was 0.134(% Conv)/HOS.

EXAMPLE 5

In Example 5, a liquid aromatic hydrocarbon having an oxygen concentration measured to be less than about 0.01 ppm by weight was contacted with a gaseous olefinic hydrocarbon in the presence of a crystalline aluminosilicate zeolite catalyst under liquid phase conditions. The purpose of Example 5 was to further evaluate the effect of the presence of oxygen on conversion and catalyst deactivation.

The catalyst, reactor, and test conditions were the same as Example 3.

The catalyst pretreatment was the same as Example 4.

The liquid aromatic hydrocarbon feed stream comprising a 50/50 volume % mixture of toluene and tetradecane was pretreatect to remove oxygen prior to starting up the reactor. The initial concentration of the oxygen in the liquid aromatic-hydrocarbon feed stream was about 15–20 ppm by weight. First, the liquid feed was sparged with a gaseous stream consisting essentially of hydrogen until the oxygen concentration was reduced to less than about 0.3 ppm oxygen. The oxygen concentration was monitored using an Orbisphere oxygen detector.

Next, the liquid feed was pumped through an oxygen adsorber and a molecular sieve for removing water. The oxygen adsorber was the Q-5 adsorber described in Example 1. The molecular sieve was of the type described in Example 1. Both adsorber units were activated by flowing 5 mole % hydrogen in nitrogen through the units at 60 ml/min while the temperature for the oxygen adsorber unit was raised to 520 deg F and the temperature for the water adsorber unit was raised to 800 deg F. Each adsorber unit was kept at these temperatures for about 10 hr. The first quantities of liquid feed through the adsorber units were discarded. The oxygen concentration of the adsorber unit effluent was less than 0.03 ppm by weight oxygen. The deoxygenated feed was collected in a product vessel. The product vessel was sealed with a silicone adhesive. The product vessel was purged with hydrogen for at least 4 hr before the deoxygenated feed was collected.

Prior to starting up the reactor, the liquid feed pump and feed lines were purged with hydrogen. Next, the liquid feed pump was flushed 4 times with the deoxygenated feed.

The reactor was then started up using the same procedure as Example 3. The results are shown in FIG. 2, run 4. The initial ethylene conversion was about 68%. After about 100 hr on stream, the ethylene conversion had dropped to about 52%. The deactivation rate for run 4 as calculated using a least squares method was as follows:

$$\% \ Conv. = 54.0 - 0.049 \ (HOS)$$

where HOS is hours on stream. The catalyst deactivation rate was 0.049(% Conv)/HOS The catalyst deactivation rate calculated for the untreated liquid aromatic hydrocarbon feed (runs 1, 2, and 3) was (0.134) (% Conv/HOS). Accordingly, removing the oxygen has the benefit of slowing catalyst deactivation by a factor of about 2.7.

We claim:

1. An aromatic alkylation process comprising the steps of purging an alkylation reactor vessel having a silica-containing molecular sieve catalyst disposed therein with an oxygen-free inert gas to reduce the oxygen concentration in said reactor to less than about 0.1 ppm, contacting an aromatic hydrocarbon having an oxygen concentration of less than about 0.1 ppm with an alkylating agent having an oxygen concentration of less than about 0.1 ppm in said reactor vessel in the presence of said catalyst under liquid phase alkylation conditions, and recovering an alkyl-substituted aromatic product from said reactor vessel.

2. A process of claim 1 wherein said aromatic hydrocarbon is at least one member selected from the group consisting of benzene, toluene, xylenes, and $C_9$ hydrocarbons.

3. A process of claim 1 wherein said alkylating agent comprises an olefinic hydrocarbon.

4. A process of claim 3 wherein said olefinic hydrocarbon comprises ethylene and propylene.

5. A process of claim 1 wherein said molecular sieve is at least one member selected from the group consisting of borosilicate, gallosilicate, chromosilicate, and aluminosilicate.

6. A process of claim 5 wherein said molecular sieve is an aluminosilicate.

7. A process of claim 6 wherein said aluminosilicate has at least one member selected from the group consisting of X, Y, L, and beta zeolite.

8. A process of claim 7 wherein said aluminosilicate is beta zeolite.

9. A process of claim 1 wherein said catalyst is employed in a plurality of porous solid containers disposed in a reactive distillation zone of said reactor vessel.

10. A process of claim 1 further comprising the steps of monitoring and regulating oxygen concentration in said reactor vessel.

11. An aromatic alkylation process comprising the steps of:
   (a) purging a reactor vessel having a silica-containing molecular sieve catalyst disposed therein with an oxygen-free inert purge gas to reduce oxygen concentration in the reactor to less than about 0.1 ppm;
(b) continuously feeding an aromatic hydrocarbon having an oxygen concentration of less than about 0.1 ppm into said reactor vessel;
(c) continuously feeding an alkylating agent into said reactor vessel;
(d) contacting said aromatic hydrocarbon with said alkylating agent in said reactor vessel in the presence of said silica-containing molecular sieve catalyst under liquid phase alkylation conditions; and
(e) recovering an alkyl-substituted aromatic product from said reactor vessel.

12. A process of claim 11 wherein said aromatic hydrocarbon is at least one member selected from the group consisting of benzene, toluene, xylenes, and $C_9$ hydrocarbons.

13. A process of claim 11 wherein said alkylating agent comprises an olefinic hydrocarbon.

14. A process of claim 13 wherein said olefinic hydrocarbon comprises ethylene and propylene.

15. A process of claim 11 wherein said molecular sieve is at least one member selected from the group consisting of borosilicate, gallosilicate, chromosilicate, and aluminosilicate.

16. A process of claim 15 wherein said molecular sieve is aluminosilicate.

17. A process of claim 16 wherein said aluminosilicate is at least one member selected from the group consisting of X, Y, L, and beta zeolite.

18. A process of claim 17 wherein said aluminosilicate is beta zeolite.

19. A process of claim 11 wherein said catalyst is employed in a plurality of porous solid containers disposed in a reactive-distillation zone of said reactor vessel.

20. A process of claim 11 wherein stop (b) further comprises the steps of monitoring and regulating oxygen concentration to maintain deowenation.

21. A process of claim 11 wherein step (c) further comprises the steps of monitoring and regulating oxygen concentration to maintain deoxygenation.

22. An aromatic alkylation process comprising the steps of:
(a) purging a reactor vessel having an alkylation catalyst comprising beta zeolite in an alumina matrix with a purge stream consisting essentially of nitrogen to reduce oxygen concentration in the reactor to less than about 0.1 ppm;
(b) continuously feeding an aromatic hydrocarbon to reduce oxygen concentration in the reactor to less than about 0.1 ppm, said aromatic hydrocarbon having an oxygen concentration of less than about 0.1 ppm, said aromatic hydrocarbon further having at least one member selected from the group consisting of benzene, toluene, xylenes, and $C_9$ hydrocarbons into said reactor vessel;
(c) continuously feeding an olefinic hydrocarbon having an oxygen concentration of less than about 0.1 ppm and comprising ethylene and propylene into said reactor vessel;
(d) contacting said aromatic hydrocarbon with said olefinic hydrocarbon in said reactor vessel in the presence of said alkylation catalyst under liquid phase alkylation conditions;
(e) recovering an alkyl-substituted aromatic product from said reactor vessel.

23. A process of claim 22 wherein said catalyst is employed in a plurality of porous solid containers disposed in a reactive-distillation zone of said reactor vessel.

24. A process of claim 22 wherein step (b) further comprises the steps of monitoring and regulating oxygen concentration to maintain deoxygenation.

25. A process of claim 22 wherein step (c) further comprises the steps of monitoring and regulating oxygen concentration to maintain deoxygenation.

26. A method of claim 1 wherein said aromatic hydrocarbon originated from a refinery stream.

* * * * *